United States Patent [19]

Wright et al.

[11] Patent Number: 4,482,564
[45] Date of Patent: Nov. 13, 1984

[54] TRIAZOLYL-SUBSTITUTED PROPANE DERIVATIVES

[75] Inventors: John J. Wright, Cedar Grove; Alan B. Cooper, West Caldwell, both of N.J.

[73] Assignee: Schering Corporation, Kenilworth, N.J.

[21] Appl. No.: 501,031

[22] Filed: Jun. 3, 1983

[51] Int. Cl.$^3$ .................... A01N 43/64; A61K 31/41; C07D 249/08
[52] U.S. Cl. .................................. 424/269; 548/262
[58] Field of Search ........................ 548/262; 424/269

[56] References Cited

FOREIGN PATENT DOCUMENTS

| 36153 | 9/1981 | European Pat. Off. ............ 548/262 |
| 48548 | 3/1982 | European Pat. Off. ............ 548/262 |
| 54974 | 6/1982 | European Pat. Off. ............ 548/341 |
| 2908378 | 9/1980 | Fed. Rep. of Germany ...... 548/262 |
| 2078719 | 1/1982 | United Kingdom ............... 548/262 |

Primary Examiner—Alton D. Rollins
Attorney, Agent, or Firm—Anita W. Magatti; Gerald S. Rosen; Bruce M. Eisen

[57] ABSTRACT

Disclosed are triazolyl-substituted propane derivatives useful in the treatment of fungal diseases of humans and animals. Also disclosed are the processes for preparing the compounds, pharmaceutical compositions containing them, and the method of treating fungal diseases with said compounds.

8 Claims, No Drawings

TRIAZOLYL-SUBSTITUTED PROPANE DERIVATIVES

SUMMARY

This invention relates to triazolyl-substituted propane derivatives useful as antifungal agents and to processes for preparing them. The invention also relates to pharmaceutical and veterinary compositions comprising the triazolyl compounds, and to methods for treating fungus diseases in humans and animals with said compositions.

DESCRIPTION OF THE INVENTION

Compounds of the invention are represented by the formula

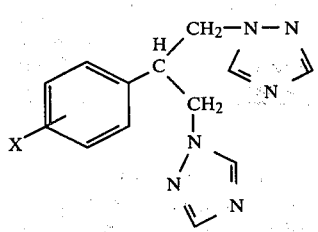

wherein X is 1-3 substituents independently selected from halogen, lower alkoxy and lower alkyl; and the pharmaceutically acceptable acid addition salts thereof.

As used herein, the term "lower alkyl" means straight or branched alkyl chains having 1 to 6 carbon atoms, e.g. methyl, ethyl, n-propyl, n-butyl, iso-butyl, pentyl and hexyl. Similarly, "lower alkoxy" means straight or branched alkoxy groups having 1 to 6 carbon atoms, e.g. methoxy, ethoxy, propoxy, iso-proxy and butoxy. The term "halogen" means chlorine, bromine or fluorine.

"Pharmaceutically acceptable acid addition salts" means those salts formed with inorganic or organic acids, e.g. hydrochloric, nitric, sulfuric, acetic, p-toluenesulfonic,, phosphoric, maleic or oxalic acid.

Preferred are compounds wherein X is 1 to 3 halogen atoms.

The present invention includes within its scope the method of eliciting an antifungal response in a human or animals, particularly warm-blooded animals, having fungal infections which comprises administering an antifungally effective amount of a compound of formula I or a pharmaceutical composition thereof.

The compounds of formula I exhibit antifungal activity against such human and animal pathogens as Candida and Trichophyton, as demonstrated by conventional in vivo tests in animals, e.g. a mouse systemic infection model. These tests indicate the compounds of this invention to be orally active. In one such test, a chronic Candida kidney infection model in mice, infected mice treated with 100 mg/kg ketoconazole (a commercially available oral antifungal agent) per day for ten days and sacrificed about 5 days after treatment ended showed a geometric mean activity of 7 colony forming units, while infected mice similarly treated with 2-(4-chlorophenyl)-1,3-di-[1-(1H-1,2,4-triazolyl)]-propane at levels of 50 mg/kg and 25 mg/kg showed geometric mean activities of 7.4 and 7.9 colony forming units, respectively. This indicates that 2-(4-chlorophenyl)-1,3-di-[(1H-1,2,4-triazolyl)]propane is approximately twice as potent as an antifungal agent as the reference compound.

Dosage level and mode of administration will vary in the judgement of the attending clinician according to the particular hose and the type and severity of infection. In general, the dosage range will be from about 100 to about 500 mg per day, in single or divided doses, with the preferred range being about 125 mg to about 250 mg per day active ingredient, combined with a suitable pharmaceutically acceptable carrier or diluent.

Also included in our invention are pharmaceutical formulations comprising an antifungally effective amount of a compound of formula I in a pharmaceutically acceptable, non-toxic carrier, preferably for oral administration. Typical oral dosage forms include tablets, capsules, elixirs, suspensions and the like. These dosage forms include typical pharmaceutically acceptable carriers, e.g. sugars such as lactose or sucrose, starches such as corn starch, cellulose and derivatives such as sodium carboxy cellulose or methyl cellulose, calcium phosphates, stearic acid, alkaline earth stearates such as magnesium stearate and polyalkylene glycols.

It is also contemplated that the antifungal compounds of this invention may be administered to animals in need of such treatment via animal feeds or in drinking water conventionally used for the animal being treated.

Compounds of the invention may be prepared as shown in the following reaction scheme:

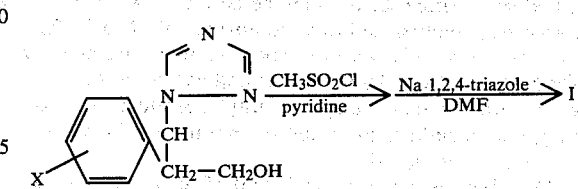

A solution of a phenyl- and triazolyl-substituted hydroxymethyl ethane of formula II in a basic solvent such as pyridine is treated with methanesulfonyl chloride, the resultant residue is then dissolved in an inert solvent such as N,N-dimethylformamide, and sodium 1,2,4-triazole is added to obtain compounds of formula I.

Starting materials of formula II are prepared by treating 1,2,4-triazole with a substituted α-bromomethylstyrene in the presence of a reducing agent such as sodium hydride, then treating the resulting triazolyl-substituted styrene with borane in a solvent such as tetrahydrofuran followed by an oxidative workup (e.g. treatment with a base such as sodium hydroxide and an oxidizing agent such as hydrogen peroxide) to produce the alcohol.

An example illustrating the preparation of compounds of this invention is given below.

EXAMPLE 1

2-(4-CHLOROPHENYL)-1,3-DI-[1-(1H-1,2,4-TRIAZOLYL)]-PROPANE

A. p-chloro-α-1H-1,2,4-triazolymethyl styrene

To a suspension of sodium hydride/oil (28 g, 0.7 mol @ 60%) in 800 ml of DMF, add in portions 1,2,4-triazole (50 g, 0.72 mol) at −10° to 0° C. Stir at 0.5° C. for 1 hour until soultion is clear brown. Add rapidly at −5° to 5° C. p-chloro-α-bromomethyl styrene (200 g, 0.86 mol total bromide, 0.56 mol allyl @ 65%). Stir and warm to room temperature over 2 hours. Evaporate off the DMF. Add saturated NaCl and extract the product with 2×300 ml of ethyl acetate. Dry the combined extracts over MgSO₄ and filter. Evaporate the ethyl acetate and chromatograph the resultant oil on 2 Waters prep. 500 cartridges using ethyl acetate:hexane (1:1) as the eluent to obtain p-chloro-α-1H-1,2,4-triazolyl-methyl styrene: HNMR (90 mHz, CDCl₃) 8.06 (1H, S), 7.93 (1H, S), 7.3 (H H, S), 5.59 (1H, S), 5.16 (3H, br S).

B.
1-(4-chlorophenyl)-1-(hydroxymethyl)-2-(1H-1,2,4-triazolyl)ethane

Dissolve the product of part A (1 g, 4.5 mmol) in 30 ml of THF and cool in an ice bath at 0° C. under a static nitrogen atmosphere. Add 14 ml of a 1 molar solution of borane in THF and let warm to room temperature. After 17 hours, destroy the excess borane with the addition of 5 ml of water. Add 10 ml of 3N sodium hydroxide and 10 ml of 30% hydrogen peroxide and let reflux. After two hours add saturated brine and extract with 3×50 ml of ethyl acetate. Dry the ethyl acetate layers over magnesium sulfate, filter and evaporate to obtain a viscous syrup. Chromatograph on 100 g of silica gel using 5% methanol/chloroform as the eluant to obtain 0.44 g (1.85 mmol, 41%) of the title compound.

C.
2-(4-chlorophenyl)-1,3-di-[1-(1H-1,2,4-triazolyl)]-propane

Dissolve the product of part B (0.44 g, 1.85 mmol) in 10 ml of pyridine. Cool in an ice bath to 0° C. and add, dropwise, methanesulfonyl chloride (0.17 ml, 2.20 mmol). Let slowly warm to room temperature and stir for 5 hours. Add 20 ml of water and extract with 3×50 ml of ethyl acetate. Dry the ethyl acetate layer over magnesium sulfate, filter and evaporate off the solvent to obtain a crude oil.

Dissolve the crude oil in 3.0 ml of N,N-dimethylformamide and add, dropwise, to a solution of sodium 1,2,4-triazole formed from the addition of triazole (0.23 g, 3.40 mmol) in 3 ml of N,N-dimethylformamide to a mixture of sodium hydride (0.08 g, 3.4 mmol) in 10 ml of N,N-dimethylformamide at 0° C. Warm and stir at 50° C. for two hours. Add 30 ml of water and extract with 3×50 ml of ethyl acetate. Dry the combined ethyl acetate layers over magnesium sulfate, filter and evaporate to dryness. Chromatograph the resulting oil on 50 g of silica gel using 5% methanol/chloroform as the eluent to obtain 0.20 g of the title compound.

In a similar manner, using appropriate starting materials, prepare the following compounds:
2-(2,4-difluorophenyl)-1,3-di-[1-(1H-1,2,4-trizolyl)]-propane;
2-(4-bromophenyl)-1,3-di-[1-(1H-1,2,4-triazolyl)]-propane;
2-(2,4-dichlorophenyl)-1,3-di-[1-(1H-1,2,4-triazolyl)]-propane;
2-(4-methylphenyl)-1,3-di-[1-(1H-1,2,4-triazolyl)]-propane;
2-(2,4-dimethylphenyl)-1,3-di-[1- (1H-1,2,4-triazolyl)]-propane;
2-(2-methyl-4-chlorophenyl)-1,3-di-[1-(1H-1,2,4-triazolyl)]-propane;
2-(2-methyl-4-fluorophenyl)-1,3-di-[1-(1H-1,2,4-triazolyl)]-propane;
2-(3,5-dichlorophenyl)-1,3-di-[1-(1H-1,2,4-triazolyl)]-propane;
2-(2-methoxy-4-fluorophenyl)-1,3-di-[1-(1H-1,2,4-triazolyl)]-propane;
2-(2-methoxy-4-methylphenyl)-1,3-di-[1-(1H-1,2,4-triazolyl)]-propane;
2-(2-methoxy-4-fluorophenyl)-1,3-di-[1-(1H-1,2,4-triazolyl)]-propane;
2-(2-fluoro-4-methylphenyl)-1,3-di-[1-(1H-1,2,4-triazolyl)]-propane;
2-(2-ethyl-4-methoxyphenyl)-1,3-di-[1-(1H-1,2,4-triazolyl)]-propane;

The following are typical pharmaceutical formulations containing as the active ingredient (designated "Drug") the compounds of this invention. The active ingredient may be 2-(4-chlorophenyl)-1,3-di-[1-(1H-1,2,4-triazolyl)]propane or an equivalent amount of any of the other compounds of this invention.

FORMULATION 1

| Tablet | 125.00 mg. tab. |
|---|---|
| Drug | 125.00 mg. |
| Polyethylene glycol 6000 | 100.00 mg. |
| Sodium lauryl sulfate | 6.25 mg. |
| Corn starch | 30.00 mg. |
| Lactose, anhydrous | 87.25 mg. |
| Magnesium stearate | 1.50 mg. |

Procedure

Heat the polyethylene glycol 6000 to 70°–80° C. Mix the drug, sodium lauryl sulfate, corn starch, and lactose into the liquid and allow the mixture to cool. Pass the solidified mixture through a mill. Blend granules with magnesium stearate and compress into tablets.

FORMULATION 2

| Capsule | 250 mg capsule |
|---|---|
| Drug | 250.00 mg. |
| Lactose, anhydrous | 100.00 mg. |
| Corn starch | 50.00 mg. |
| Microcrystalline cellulose | 95.00 mg. |
| Magnesium stearate | 5.00 mg. |

Procedure

Mix the first four ingredients in a suitable mixer for 10–15 minutes. Add the magnesium stearate and mix for 1–3 minutes. Fill the mixture into suitable two-piece hard gelatin capsules using an encapsulating machine.

We claim:

1. A compound represented by the formula

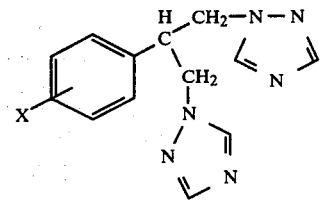

wherein X is 1 to 3 substituents independently selected from halogen, lower alkoxy and lower alkyl; and the pharmaceutically acceptable salts thereof.

2. A compound of claim 1 wherein X is 1 to 3 halogen atoms.

3. A compound of claim 2 wherein X is fluorine or chlorine.

4. A compound of claim 1 which is 2-(4-chlorophenyl)-1,3-di-[1-(1H-1,2,4-triazolyl)]propane.

5. A compound of claim 1 which is 2-(2,4-difluorophenyl)-1,3-di-[1-(1H-1,2,4-triazolyl)]propane.

6. A composition useful for inhibiting the growth of fungi in a human or animal having a fungal infection which comprises an antifungally effective amount of a compound of claim 1 in admixture with a pharmaceutically acceptable carrier.

7. A composition according to claim 9 which is suitable for oral use.

8. A method of inhibiting the growth of fungi which comprises administering to an animal or human having a fungal infection a composition of claim 6.

* * * * *